United States Patent [19]

Tsuda et al.

[11] 4,374,981

[45] Feb. 22, 1983

[54] ULTRAFILTRATION OF FERMENTATION BROTH CONTAINING NUCLEOSIDES TO SEPARATE INOSINE AND GUANOSINE FROM THE BROTH

[75] Inventors: Masahiko Tsuda, Kobe; Kazuhiko Ohta, Ikeda; Kiyoshi Nara, Kyoto, all of Japan

[73] Assignee: Takeda Chemical Industries, Ltd., Osaka, Japan

[21] Appl. No.: 323,705

[22] Filed: Nov. 20, 1981

[30] Foreign Application Priority Data

Nov. 27, 1980 [JP] Japan ............................... 55-167667

[51] Int. Cl.$^3$ ...................... C07H 17/00; C07H 19/06
[52] U.S. Cl. ......................................... 536/24; 536/26
[58] Field of Search ..................................... 536/24, 26

[56] References Cited

U.S. PATENT DOCUMENTS 3,238,252 3/1966 Giacometti ........................... 536/24

FOREIGN PATENT DOCUMENTS 42-12432 7/1967 Japan ..................................... 536/24
42-15114 8/1967 Japan ..................................... 536/24
52-148683 12/1977 Japan .

*Primary Examiner*—Nicky Chan
*Attorney, Agent, or Firm*—Wenderoth, Lind & Ponack

[57] ABSTRACT

Inosine and/or guanosine can be separated from fermentation broth containing microbial cells and high-molecular-weight substances by heat-treating said broth at 90° to 110° C., followed by subjecting to ultrafiltration. The present process is advantageously carried out in the industrial use of ultrafiltration.

2 Claims, No Drawings

ULTRAFILTRATION OF FERMENTATION BROTH CONTAINING NUCLEOSIDES TO SEPARATE INOSINE AND GUANOSINE FROM THE BROTH

The present invention relates to a method of separating advantageously nucleosides, i.e. inosine, guanosine or both of them in a fermentation broth by subjecting to ultrafiltration.

Normally, it is well known that, in advance of separating and recovering particular low-molecular-weight products from a fermentation broth, suspended solids contained in the fermentation broth, such as microbial cells, their fragments, proteins and fine particles contained originally in culture media and raw materials should be separated and removed, thereby facilitating subsequent purification steps. As the industrially applicable means of removing such suspended solids, there have been conventionally employed vacuum filtration, pressure filtration and centrifugation. In recent years, micro filtration and ultrafiltration with use of membranes based on a variety of high molecular compounds are being put to practical use. Among these, the ultrafiltration method offers the unique characteristics in that said method, with its optimal membrane selected, can remove not only microbial cells and other suspended solids but also soluble, high-molecular-weight contaminants such as proteins, peptides, polysaccharides and other colloidal substances. Nevertheless, depending on type of fermentation broths the ultrafiltration method, in spite of such characteristics, has not yet come to applied for industrial purpose.

The present inventors found that when the ultrafiltration method was applied in separating inosine and guanosine, which find useful application as starting substances for a flavor nucleotide, etc., from a fermentation broth containing such substances, the flux rate began to decrease greatly within a very short period of time, and that said method cannot be adopted on an industrial scale. Such decrease in flux rate is thought to be attributable to the following:

Inosine and guanosine exhibit lowered solubility in water, and in order to subject a fermentation broth containing such substances to ultrafiltration, therefore, it is required to raise the liquid temperature and to increase the amount of such substances dissolved in the fermentation broth so that the liquid quantity to be treated may be able to be reduced to a desirable extent. For example, warming at temperatures in the range of 60° to 80° C. must be done in the case of the concentrations of inosine or guanosine as shown in the examples to be described hereinafter.

Under a temperature as high as 60° to 80° C., however, a much greater proportion of high-molecular-weight substances within microbial cells such as proteins and polysaccharides are often eluted out of the cells than at ambient temperature, whereby such high-molecular-weight substances cause the so called concentration polarization to occur on membrane surfaces; this results in the formation of gel layers with reduced specific permeability, which is considered to decrease the flux rate. When ultrafiltration is carried out on an industrial scale while leaving such problem unsolved, ultrafiltration equipment with large membrane surface area will become necessary, with increased costs of installation and of cleaning membranes to be incurred, and it is evident that the best use cannot be made of the advantages of the ultrafiltration method.

The present inventors, in view of the situation mentioned above, conducted extensive investigation on putting into practical use of the ultrafiltration method intended for use in fermentation broth containing inosine and/or guanosine and, as a result, have completed the present invention.

Thus, the present invention relates to a process of separating inosine, guanosine or their mixture from microbial cells and high-molecular-weight substances, characterized in that said process comprises heating a fermentation broth containing inosine, guanosine or both of them at 90° to 110° C., followed by subjecting to ultrafiltration.

In the present invention, under "fermentation broth containing inosine, guanosine or both of them" (hereinafter referred to, in some instances, briefly as "fermentation broth") is to be understood as a fermentation broth obtained by cultivating a microorganism capable of producing these substances, and it may be broth as such after the completion of fermentation or that further diluted with water, as the case may be. As examples of microorganism, there may be mentioned *Bacillus subtilis* ATCC 19221, *Bacillus subtilis* ATCC 13956 (IFO 14124), *Bacillus pumilus* No. 148-S-16 (IFO 12483), *Bacillus pumilus* No. 158-A-17 (IFO 12477), *Brevibacterium ammoniagenes* ATCC 21477, *Brevibacterium ammoniagenes* ATCC 21478, *Brevibacterium ammoniagenes* ATCC 21479, *Brevibacterium ammoniagenes* ATCC 21480 and so on.

Said fermentation broth is then heated until it reaches 90° to 110° C., preferably 95° to 105° C. The purpose of such heating lies in causing high-molecular-weight substances, such as proteins or polysaccharides, which originate from microbially cells in the fermentation broth and contribute to lowering the flux rate due to concentration polarization occurring on the surface of the membrane during ultrafiltration, to be adequately aggregated. The high-molecular-weight substances thus aggregated adequately do not cause the flux rate to drop any more. The heat-treating temperature of not higher than 90° C. results in inadequate aggregation of high-molecular-weight substances, and that of not lower than 110° C., at which the broth gets extremely colored, is not desirable. The heat-treating time is not particularly limited, only if a length of time is allowed enough to aggregate adequately high-molecular-weight substances in the fermentation broth but not to bring about too much coloration of the broth and the like. Normally, heat-treating time is in the range of about 10 minutes at 90° C. and about 5 minutes at 110° C.

After being heat-treated, the fermentation broth is preferably cooled as soon as possible to a temperature at which ultrafiltration is performed, or to lower temperatures, and this can prevent excessive coloration of the broth. Normally, the pH of the fermentation broth on the occasion of heat treatment is preferably 5.5 to 9.0, and needs not be particularly adjusted, if the pH of the liquor after the completion of cultivation is 5.5 to 9.0.

The fermentation broth is then subjected to ultrafiltration, whereupon the ultrafiltration method per se is conducted into practice following the known processes. As the temperature during ultrafiltration, there are employed temperatures at which inosine and guanosine contained in the fermentation broth get well dissolved, and specifically, such temperatures are determined by contents of these substances in the fermentation broth.

Normally, such temperatures are appropriately selected from the temperature range of about 40° to 85° C., and it is preferred to conduct ultrafiltration into practice at about 70° to 85° C. when guanosine having a higher temperature of dissolution of crystals is contained.

Materials for ultrafiltration membranes may be those that are commercially available, but heat-resistant materials are selected for fermentation broth with a higher content of guanosine, because ultrafiltration must be performed at increased temperatures of 70° to 85° C. at which such crystals dissolve. As the relatively heat-resistant material, there may be suitably used polysulfones, polyamides, and the like. As the module type, there may be employed any of plate type, tubular type, spiral wound type and hollow fiber type, and the module types having a simple structure such as plate type and tubular type are normally preferred, because the fermentation broth shows a greater concentration of suspended solids and an increased viscosity as the filtration and concentration progress. The molecular weight cut-off of membranes to fractionate may be not less than 1000, in view of the molecular weights of inosine and guanosine, and in practice, is preferably in the range of about 5000 to 300000 in order to assure greater flux rate.

Inosine, guanosine or their mixture thus separated from microbial cells and high-molecular-weight substances is subjected to the purification step in accordance with conventional processes, as the case may be.

According to the method of the present invention, the ultrafiltration method can be applied favorably on an industrial scale in separating inosine, guanosine or both of them from a fermentation broth containing these substances. That is to say, said fermentation broth heat-treated by means of the method of the present invention can be subjected to ultrafiltration, whereby a decrease in the volume of permeate per unit time is prevented over a by far prolonged period of time as compared with the case of a fermentation broth without heat treatment, and working efficiency is greatly improved. The method of the present invention enables ultrafiltration to be utilized on an industrial scale, and this results in eliminating the necessity of using filter aids as is the case with the pressure filtration method mainly adopted in the past and consequently in bringing about no production of large amounts of wastes. Furthermore, the method offers the advantage of extremely improved processability as compared with the centrifugation method.

The examples are given below to illustrate the present invention in more detail.

EXAMPLE 1

Into two equal parts of 250 ml was divided 500 ml of the fermentation broth (inosine; 4.2 g/l, guanosine; 5.6 g/l, pH 6.7) obtained by inoculating with a culture of *Bacillus subtilis* ATCC 19221 a culture medium (pH 7.2) composed of 8% of glucose, 0.1% of magnesium sulfate, 0.01% of ferrous sulfate, 0.01% of manganese sulfate, 2.0% of ammonium nitrate, 0.2% of potassium hydrogenphosphate, 0.01% of potassium chloride, 0.15% of ribonucleic acid, 1.2% of monosodium glutamate, 1.5% of calcium carbonate, 4% (weight/volume) of corn steep liquor, 0.03% of histidine, 0.03% of arginine and 0.03% of methionine, followed by incubating for 72 hr. at 34° C. One of them was heated for 5 minutes at 110° C. and then cooled, while the other as such was used as a control. These fermentation broths were each subjected to ultrafiltration by means of a ultrafilter type MC-4 fitted with Diafilter A-50T (76 m/m$\phi$, 50,000 of the molecular weight cut-off) produced by Bioengineering Co., Ltd. (Japan) under the conditions of 60° C., 2 kg/cm$^2$ and 1,300 rpm of number of revolution of agitator of a magnetic stirrer. The relationship between the filtration time and the amount of permeated liquid as observed is shown in Table 1.

TABLE 1

| Filtration time, hr. | Amount of permeate, ml | |
|---|---|---|
| | Fermentation broth (A) | Fermentation broth (B) |
| 1 | 85 | 50 |
| 3 | 145 | 85 |
| 5 | 195 | 112 |
| 9 | 228 | 130 |

Note:
Fermentation broth (A): Heat-treated for 5 min. at 110° C.
Fermentation broth (B): Not heat-treated (control)

As is obvious from Table 1, it was observed that the fermentation broth (A) treated by the method of the present invention displays a by far increased flux rate as compared with the control of the fermentation broth (B).

EXAMPLE 2

Into two equal parts of 250 ml was divided 500 ml of the fermentation broth (inosine 4.3 g/l, guanosine 5.9 g/l, pH 7.0) obtained by cultivating the microorganism of Example 1, and one of them was heat-treated for 10 minutes at 90° C., while the other as such without heat treatment was used as a control. Both of them were subjected to ultrafiltration with use of the same ultrafiltration equipment as in Example 1 under the conditions of 80° C., 2 kg/cm$^2$ and 1300 rpm of number of revolution of agitator of a magnetic stirrer, and the relationship between the filtration time and the amount of permeate was compared. The results are shown in Table 2.

TABLE 2

| Filtration time, hr. | Amount of permeate, ml | |
|---|---|---|
| | Fermentation broth (A') | Fermentation broth (B') |
| 1 | 97 | 45 |
| 3 | 152 | 82 |
| 5 | 210 | 106 |
| 9 | 238 | 130 |

Note:
Fermentation broth (A'): Heat-treated for 10 min. at 90° C.
Fermentation broth (B'): Not heat-treated (control)

As is obvious from Table 2, it is understood that the fermentation broth (A') treated by the method of the present invention exhibits a by far increased flux rate as compared with the control of the fermentation broth (B').

EXAMPLE 3

A seed culture, which was obtained by inoculating with a culture of *Bacillus subtilis* ATCC 19221 50l of a culture medium (pH 7.2) composed of 8% of glucose, 0.1% of magnesium sulfate, 0.01% of ferrous sulfate, 0.01% of manganese sulfate, 2.0% of ammonium nitrate, 0.2% of potassium hydrogenphosphate, 0.01% of potassium chloride, 0.15% of ribonucleic acid, 1.2% of monosodium glutamate, 1.5% of calcium carbonate, 4% (weight/volume) of corn steep liquor, 0.03% of histidine, 0.03% of arginine and 0.03% of methionine, and incubating it for 24 hrs. at 34° C., was transferred to 750 l of the culture medium of the same composition, followed by incubating for 72 hrs. at 34° C. 500 l of the resultant fermentation broth (containing 4.5 g/l of inosine and 5.7 g/l of guanosine) was divided into two equal parts of 250 l, and one of them was heated for 10 minutes at 100° C., while the other as such without heat-treatment was used as a control. The heat-treated fermentation broth and the control fermentation broths as described above were each subjected to ultrafiltration in the batch process, for the comparative study, by means of a ultrafiltration equipment which consisted of a 300-l capacity tank for concentrated liquid and a circulating pump coupled with two pieces of tubular type membranes of 1-inch inner diameter (PS-150, produced by Kanegafuchi Chemical Industry Co., Ltd. (Japan), with 0.1 m$^2$ of membrane surface area per piece). Ultrafiltration was continued at 80° C. of filtration temperature, 125 l/min of circulating flow rate and 2.0 kg/cm$^2$ gauge of pressure until 200 l of permeate was obtained. Ultrafiltration of the heat-treated fermentation broth commenced at the flux rate of 50 l/hr, progressed at 40 l/hr after 2 hours, and yielded 200 l of permeated liquid over a period of 4.5 hours. On the other hand, ultrafiltration of the fermentation broth not heated commenced at the flux rate of 35 l/hr, progressed at 22 l/hr after 2 hours and required 14 hours to produce 200 l of permeate.

What we claim is:

1. A process for separating inosine, guanosine or their mixture from a fermentation broth, which comprises heat-treating said fermentation broth at 90° to 110° C., followed by subjecting thus-heated fermentation broth to ultrafiltration.

2. A process according to claim 1, wherein the heat-treatment is conducted at 95°–105° C.

* * * * *